United States Patent
Shirvan et al.

(10) Patent No.: US 8,288,442 B2
(45) Date of Patent: Oct. 16, 2012

(54) USE OF DERIVATIVES OF VALPROIC ACID AMIDES AND 2-VALPROENIC ACID AMIDES FOR THE TREATMENT OR PREVENTION OF PAIN AND/OR HEADACHE DISORDERS

(75) Inventors: Mitchell Shirvan, Hertzleya (IL); Meir Bialer, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 12/457,875

(22) Filed: Jun. 24, 2009

(65) Prior Publication Data
US 2009/0281045 A1 Nov. 12, 2009

Related U.S. Application Data

(63) Continuation of application No. 10/826,904, filed on Apr. 16, 2004, which is a continuation of application No. 09/932,370, filed on Aug. 17, 2001, now abandoned.

(60) Provisional application No. 60/225,973, filed on Aug. 17, 2000, provisional application No. 60/225,977, filed on Aug. 17, 2000.

(51) Int. Cl.
*A61K 31/16* (2006.01)
(52) U.S. Cl. ........ 514/616; 514/625
(58) Field of Classification Search .......... 514/616, 514/625
See application file for complete search history.

*Primary Examiner* — San-Ming Hui
(74) *Attorney, Agent, or Firm* — Browdy and Neimark, PLLC

(57) ABSTRACT

A method for the treatment or prevention of pain and/or a headache disorder using a derivative of a valproic acid amide or a 2-valproenic acid amide, as well as pharmaceutical compositions comprising these derivatives or compounds.

12 Claims, 1 Drawing Sheet

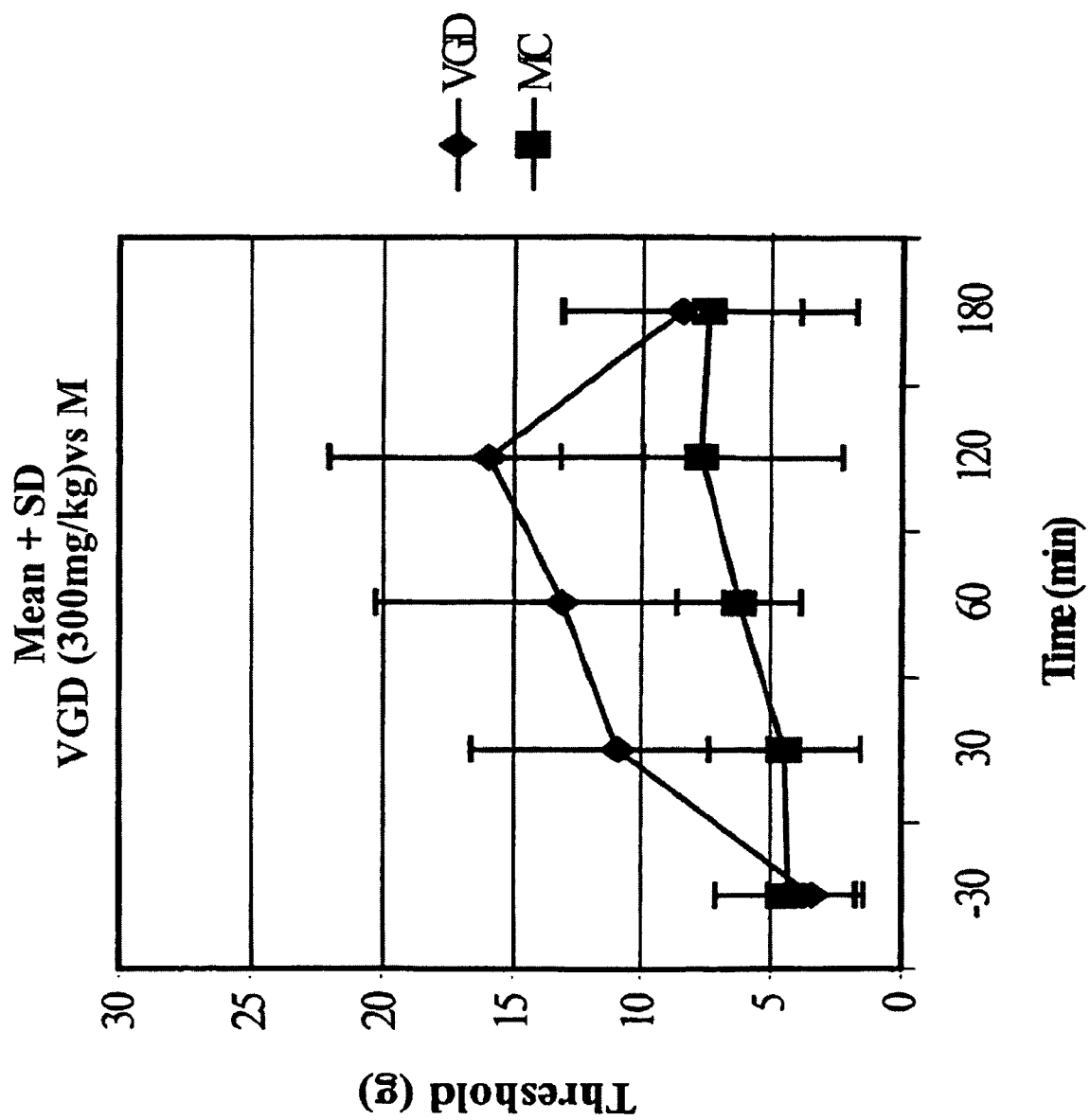

ium channel blockers; anti-depressants; and anti-epileptic
USE OF DERIVATIVES OF VALPROIC ACID AMIDES AND 2-VALPROENIC ACID AMIDES FOR THE TREATMENT OR PREVENTION OF PAIN AND/OR HEADACHE DISORDERS This application is a Continuation of U.S. application Ser. No. 10/826,904, filed Apr. 16, 2004, which is a Continuation of U.S. application Ser. No. 09/932,370, filed Aug. 17, 2001, an application claiming the benefit under 35 USC 119(e) of U.S. Provisional Application No. 60/225,973, filed Aug. 17, 2000, and claiming the benefit under 35 USC 119(e) of U.S. Provisional Application No. 60/225,977, filed Aug. 17, 2000, the entire content of each of which is hereby incorporated herein by reference in its entirety.

Throughout this application, various references are referenced by short citations within parenthesis. Full citations for these references may be found at the end of the specification, immediately preceding the claims. These references, in their entireties, are hereby incorporated by reference to more fully describe the state of the art to which this invention pertains.

FIELD OF THE INVENTION

Disclosed is a method for the treatment or prevention of pain and/or headache disorders, such as migraines, using derivatives of valproic acid amides and 2-valproenic acid amides.

BACKGROUND OF THE INVENTION

Pain is considered to play a basic physiological role in the detection and localization of tissue damage or potentially damaging physiological processes. Pain has been broadly classified as somatogenic, where a physiological explanation can be found, or psychogenic, where the physiological explanation is not known (The Merck Manual of Diagnosis and Therapy).

One example of a somatogenic pain is neuropathic pain. Generally, neuropathic pain is described as a pain which results from a dysfunction in the central or peripheral nervous system (Tremont-Lukats, I. et al.; Woolf, C. and Mannion, R.).

The pain can be both chronic and acute, and can also be evoked by noxious stimuli, also referred to as hyperalgesia, or by non-noxious stimuli referred to as allodynia (Attal, N.). Allodynia and hyperalgesia can have mechanical causes (dynamic or static), or a thermal cause. Examples of neuropathic pain include: all the painful peripheral neuropathies and specifically diabetic peripheral neuropathy; postherpetic neuralgia; and trigemincal neuralgia. Trigeminal neuralgia, for example, is the most common neuralgic syndrome in the elderly. The initial drug of choice is carbamazepine. For other types of pain, such as postherpetic neuralgia and painful diabetic neuropathy, amitriptyline is most commonly used. Other types of somatogenic pain that may have neuropathic components include cancer pain, postoperative pain, low back pain, complex regional pain syndrome, phantom pain, HIV pain, arthritis (osteo-arthritis and rheumatoid arthritis) pain and migraines.

Pain may also be a symptom of headache disorders. Migraines constitute one of the four major categories of primary headaches (International Headache Society; Silberstein, S. D. et al.). The other three types of primary headaches are tension-type, cluster and a miscellaneous-type (International Headache Society; Silberstein, S. D. et al.). One current view is that there is a continuous spectrum of headache severity ranging from mild tension headaches to severe migraines. Others consider tension headaches and migraines to be distinct entities.

Migraines are considered to be a familial disorder characterized by periodic pulsatile headaches. (Principles of Neurology). Migraines are found in about 4% of the male population and 7% of the female population. Migraines can occur in the presence or absence of an aura. An aura is a complex of focal neurological symptoms which may precede or accompany a migraine attack (Silberstein, S. D. et al.). Auras can be characterized by visual, sensory, or motor phenomenon, and may also involve language or brainstem disturbances (Silberstein, S. D. et al.).

A major theory regarding the pain of migraines is that it stems from a form of sterile neurogenic inflammation (Moskowitz, M. A. and Cutrer, F. M.). The neurogenic inflammation results in the leakage of plasma proteins into the dura mater, which can be quantified by measuring the leakage of radioactive albumin (Suzzi, M. C. and Moskowitz, M. A.).

Drugs used in the treatment of headache disorders such as migraines originate from a broad range of different drug categories. These include: 5-hydroxytryptamine agonists (5-HT$_1$ agonists); dihydroergotamine; ergotamine; anti-emetics; anxiolytics; non-steroidal anti-inflammatory drugs; steroids; major tranquilizers; narcotics; beta-blockers; calcium channel blockers; anti-depressants; and anti-epileptic drugs. However, not all of the drugs in these categories are truly effective. Considering all of the drugs which are effective, there is still a need for more efficacious drugs, as well as anti-migraine treatments with less side effects.

U.S. Pat. No. 5,585,358 describes a series of derivatives of valproic acid amides and 2-valproenic acid amides for the treatment of epilepsy and other neurological disorders. However, U.S. Pat. No. 5,585,358 does not teach or suggest the use of derivatives of valproic acid amides and 2-valproenic acid amides for the treatment or prevention of pain or headache disorders.

SUMMARY OF THE INVENTION

The subject invention provides a method of treating or preventing pain and/or a headache disorder in a subject comprising the administration of a therapeutically effective amount of a derivative of a valproic acid amide or a 2-valproenic acid amide, to thereby treat or prevent the pain and/or headache disorder. In addition, the subject invention contains pharmaceutical compositions comprising these derivatives.

DESCRIPTION OF THE DRAWINGS

FIG. 1 presents the effects of the administration of VGD (valproylglycine amide or Compound 1) versus MC (methyl cellulose or vehicle) in the Chung model of neuropathic pain.

DETAILED DESCRIPTION OF THE INVENTION

The subject invention provides a method of treating subject suffering from pain comprising periodically administering to the subject a therapeutically effective amount of a compound having the following structure:

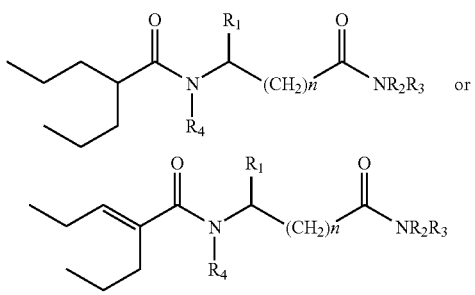

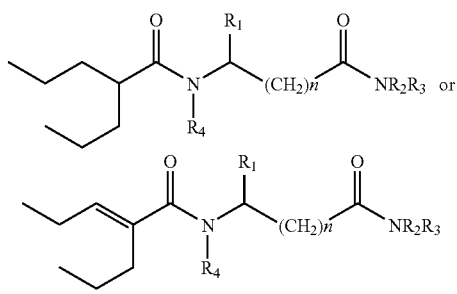

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby treat the subject's pain.

The subject invention also provides a method of preventing pain in a subject predisposed to suffering from pain comprising periodically administering to the subject a prophylactically effective dose of a compound having the following structure:

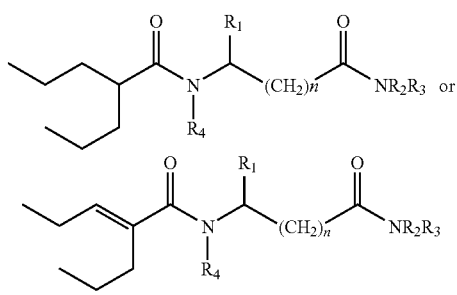

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby prevent pain in the subject.

In addition, the subject invention provides a method of treating a subject suffering from a headache disorder comprising periodically administering to the subject a therapeutically effective dose of a compound having the following structure:

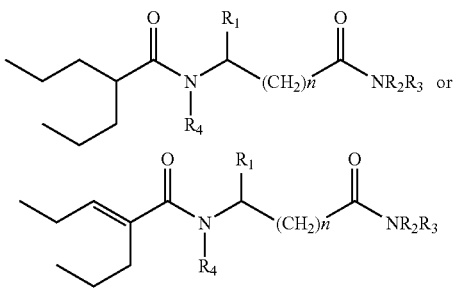

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby treat the headache disorder.

The subject invention further provides a method of preventing a headache disorder in a subject predisposed to suffering from a headache disorder comprising periodically administering to the subject a prophylactically effective dose of a compound having the following structure:

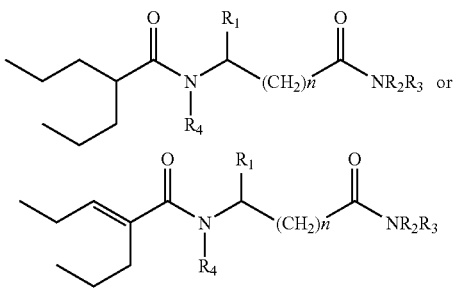

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby prevent the headache disorder in the subject.

In one embodiment, the compound has the following structure:

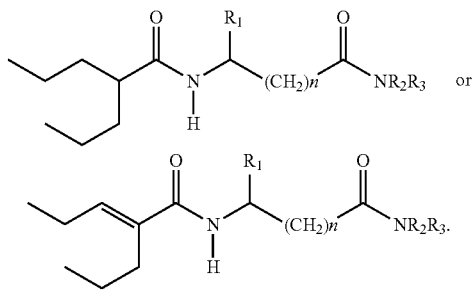

In an additional embodiment, the compound is N-(2-n-propylpentanoyl)-glycinamide and has the structure:

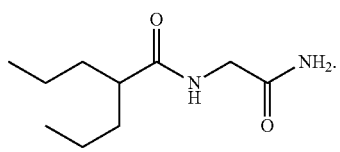

In another embodiment, the compound is N-(2-n-propyl-pent-2-enoyl)-glycinamide and has the structure:

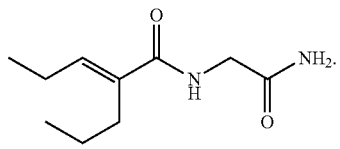

In one embodiment, the pain is acute. In another embodiment, the pain is chronic. In a further embodiment, the pain is somatogenic pain. In a preferred embodiment, the pain is neuropathic pain.

The headache disorder may be a migraine.
The headache disorder may be a cluster headache.
The headache disorder may be a tension-type headache.
The headache disorder may be a miscellaneous-type headache.

The subject may be a human being.

In one embodiment, one or more of $R_1$, $R_2$, $R_3$, or $R_4$ is a linear chain $C_1$-$C_6$ alkyl group. In another embodiment, one or more of $R_1$, $R_2$, $R_3$, or $R_4$ is a branched chain $C_1$-$C_6$ alkyl group. In yet another embodiment, one or more of $R_1$, $R_2$, $R_3$, or $R_4$ is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group. In still another embodiment, one or more of $R_1$, $R_2$, $R_3$, or $R_4$ is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

The subject invention also provides a method of treating a subject suffering from neuropathic pain comprising administering to the subject 500 mg of N-(2-n-propylpentanoyl)glycinamide six times per day so as to thereby treat the subject's neuropathic pain.

In addition, the subject invention provides a method of preventing neuropathic pain in a subject predisposed to suffering from neuropathic pain comprising administering to the subject 500 mg of N-(2-n-propylpentanoyl)glycinamide six times per day so as to thereby prevent neuropathic pain in the subject.

Some of the compounds used in this invention possess chiral centers. It is a further embodiment of this invention that these compounds may comprise substantially pure D or L enantiomers or racemic mixtures. It is to be understood that compounds of this invention may be of the E-(trans) or Z-(cis) geometric configuration, or a mixture thereof.

In the practice of the invention, the amount of the compound incorporated in the pharmaceutical composition may vary widely. Factors considered when determining the precise dose are well known to those skilled in the art. Examples of such factors include, but are not limited to, the subject being treated and the specific pharmaceutical carrier, as well as the route and frequency of administration.

A therapeutically effective dose of the compound may comprise about 10 to about 6,000 mg of the active ingredient. In one embodiment, the therapeutically effective dose comprises about 10 to about 3,000 mg. In another embodiment, the therapeutically effective dose comprises about 10 to about 2,000 mg. In a preferred embodiment, the therapeutically effective dose comprises about 10 to about 1,000 mg of the active ingredient. In another embodiment, the therapeutically effective dose comprises about 50 mg to about 500 mg. In a further embodiment, the therapeutically effective dose comprises about 500 to about 4000 mg. In another embodiment, the therapeutically effective dose comprises about 1000 to about 3000 mg. In yet another embodiment, the therapeutically effective dose comprises about 2000 to about 3000 mg. In a preferred embodiment, the therapeutically effective dose comprises about 3000 mg.

A prophylactically effective dose of the compound may comprise about 10 to about 6,000 mg of the active ingredient. In one embodiment, the prophylactically effective dose comprises about 10 to about 3,000 mg. In another embodiment, the prophylactically effective dose comprises about 10 to about 2,000 mg. In a preferred embodiment, the prophylactically effective dose comprises about 10 to about 1,000 mg of the active ingredient. In another embodiment, the prophylactically effective dose comprises about 50 mg to about 500 mg. In a further embodiment, the prophylactically effective dose comprises about 500 to about 4000 mg. In another embodiment, the prophylactically effective dose comprises about 1000 to about 3000 mg. In yet another embodiment, the prophylactically effective dose comprises about 2000 to about 3000 mg. In a preferred embodiment, the prophylactically effective dose comprises about 3000 mg.

The administration of the compound may be effected once daily or up to 6 times per day. Thus, in one embodiment, the administration of the compound may be effected twice a day. In another embodiment, the administration of the compound may be effected 3 times a day. In a further embodiment, the administration of the compound may be effected 4 times a day. In yet another embodiment, the administration of the compound may be effected 5 times a day. In an added embodiment, the administration of the compound may be effected 6 times a day.

The subject invention also provides a method of treating a subject suffering from pain comprising periodically administering to the subject a therapeutically effective dose of composition comprising a compound having the following structure:

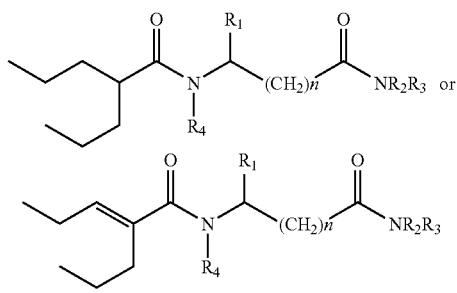

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby treat the subject's pain.

Additionally, the subject invention provides a method of preventing pain in a subject predisposed to suffering from pain comprising periodically administering to the subject a prophylactically effective dose of composition comprising a compound having the following structure:

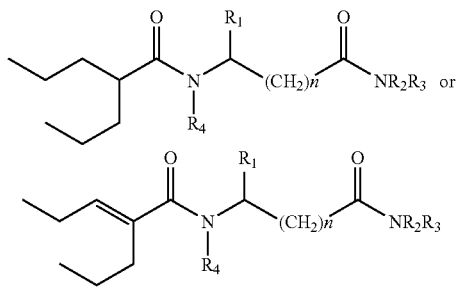

wherein $R_1$, $R_2$, $R_3$ and $R_4$ are independently the same or different and are hydrogen, a linear or branched $C_1$-$C_6$ alkyl group, an aralkyl group, or an aryl group, and n is an integer which is greater than or equal to 0 and less than or equal to 3, so as to thereby prevent pain in the subject.

The subject invention also provides compounds containing a valproic acid moiety or a 2-valproenic acid moiety, as well as pharmaceutical compositions comprising these compounds.

The subject invention further provides a pharmaceutical composition comprising the compound and a pharmaceutically acceptable carrier. As used herein, the term "pharmaceutically acceptable carrier" encompasses any of the standard pharmaceutically accepted carriers, such as a phosphate-buffered saline solution, water, suspensions, powders, emulsions such as an oil/water emulsion or a triglyceride emulsion, various types of wetting agents, tablets, coated tablets, dissolvable tablets and capsules. An example of an acceptable triglyceride emulsion useful in the intravenous and intraperitoneal administration of the compounds is the triglyceride emulsion commercially known as Intralipid®.

Typically, pharmaceutically acceptable carriers contain excipients such as starch, milk, sugar, certain types of clay, gelatin, stearic acid, talc, vegetable fats or oils, gums, glycols, or other known excipients. These carriers may also include flavor and color additives or other ingredients.

In the practice of the invention, the administration of the pharmaceutical composition may be effected by any of the well known methods including, but not limited to, by inhalation, rectal, oral, intravenous, intraperitoneal, parenteral, intramuscular, transdermal, subcutaneous, sublingual, nasal, buccal, pulmonary, vaginal or topical administration.

Topical administration can be effected by any method commonly known to those skilled in the art. These methods include, but are not limited to, incorporation of the pharmaceutical composition into creams, gels, ointments, transdermal patches or other topical formulations and delivery systems.

When the compound is introduced orally, it may be mixed with other food forms and consumed in solid, semi-solid, suspension or emulsion form. The compound may be administered as sprinkles. In one embodiment, the oral composition may be enterically-coated. Use of enteric coatings are well known in the art. Commonly known enteric coatings include Eudragit S and Eudragit L (Lehman, K., 1971; Lehman, K. 1973; Handbook of Pharmaceutical Excipients, $2^{nd}$ ed.).

The invention encompasses a pharmaceutical composition as hereinabove described wherein the carrier is a solid and the composition is a tablet. The invention also encompasses a pharmaceutical composition as hereinabove described wherein the carrier is a gel and the composition is a suppository. The invention further encompasses a pharmaceutical composition as hereinabove described wherein the carrier is a liquid and the composition is a solution.

The following Experimental Details are set forth to aid in an understanding of the invention, and are not intended, and should not be construed, to limit in any way the invention set forth in the claims which follow thereafter.

EXPERIMENTAL DETAILS

I. Synthesis of Compounds

Compound 1 N-(2-n-propylpentanoyl)glycinamide

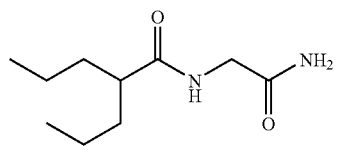

Compound 1 was prepared as disclosed by U.S. Pat. No. 5,585,358.

Compound 2
N-(2-n-propylpent-2-enoyl)glycinamide

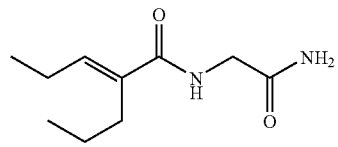

Compound 2 was prepared as disclosed by U.S. Pat. No. 5,585,358.

II. Experimental Examples

Example 1

The anti-pain effects of Compounds 1 and 2 are evaluated in a model for traumatic nerve injury. The specific model is the rat constriction injury model, a commonly accepted model for the evaluation of the potential of a compound to treat chronic neuropathic pain. The end point is whether a compound can reverse cold allodynia in rats following a neuropathic injury. MC may be used as the control.

Results

Compounds 1 and 2 reverse cold allodynia in the chronic constriction injury model of neuropathic pain with $ED_{50}$ values of less than 500 mg/kg. The effective dose is below that which has been previously found to be the median ataxic dose (also referred to as the minimal neurotoxic dose). MC may be used as the control.

Discussion

The results indicate that Compounds 1 and 2 are effective for the treatment of pain. Thus, the disclosed valproic acid amides and 2-valproenic acid amides are effective for the treatment or prevention of pain, including neuropathic pain.

Example 2

The potential of Compound 1 to serve as an anti-pain agent was studied in the Chung model (Kim, S. H. and Chung, J. M.). This model is known as a reliable model, predictive for human pain. (Kim, S. H. and Chung, J. M.). In this model, spinal nerves L5 and L6 of the rat are tightly ligated and cut in order to induce neuropathic pain. Male Sabra rats weighing 250-275 g were used throughout the study. Under xylazine-ketamine anesthesia, both the L5 and L6 spinal nerves of one side of the rat were tightly ligated and cut. Pain behavior was measured following operation in all groups using withdrawal latencies of the hind paw to mechanical stimulation with von Frey filaments (tactile allodynia). The mechanical sensitivity of the foot was quantified by the occurrence of foot withdrawal in response to normally innocuous mechanical stimuli. Eight different von Frey filaments ranging from 0.6 to 26 g were used.

The efficacy (antiallodynic effect) of the compound was evaluated (300 mg/kg, per os (oral)) in eight rats at days 7 and 14 postoperation in a double-blind randomized crossover manner. The testing included estimation of time of peak effect following drug administration and measurement of the ability of the compound to decrease tactile allodynia.

Results

The compound reversed tactile allodynia in the Chung model in comparison to vehicle (MC-methyl cellulose). It was found that the compound reversed the tactile allodynia and therefore, the hind paw withdrawal occurred at higher thresholds. The time of peak effect was 60 minutes. At a statistically significant level, the compound prevented tactile allodynia when compared to vehicle 60 minutes (p=0.0207) and 120 minutes (p=0.0102) following drug administration (Mann-Whitney test). The results are shown in FIG. 1.

Discussion

The results demonstrated that Compound 1 is effective for the treatment of pain. Thus, the disclosed valproic acid amides are effective for the treatment or prevention of pain, including neuropathic pain.

Example 3

Evaluation of the anti-headache effects of Compounds 1 and 2 are followed in the migraine model of Moskowitz (Suzzi, M. C. and Moskowitz, M. A.). In this model, neurogenic inflammation results in the leakage of plasma proteins into the dura matter (plasma protein extravasation), which can be quantified by measuring the leakage of radioactive albumin (Suzzi, M. C. and Moskowitz, M. A.).

Results

The results of the experiment employing Compounds 1 and 2 separately are displayed in Table 1. Individually, Compounds 1 and 2 inhibit plasma protein extravasation as compared to the control group (Table 1).

TABLE 1

Inhibition of Plasma Protein Extravasation by Compounds 1 and 2

|  | Control | Compound 1 | Compound 2 |
|---|---|---|---|
| Percent Extravasation Compared to Control | 100 | <100 | <100 |

Discussion

The Moskowitz model, which is a well-accepted model of migraines (Suzzi, M. C. and Moskowitz, M. A.), shows that Compounds 1 and 2 inhibit plasma protein extravasation. Thus, the disclosed valproic acid amides and 2-valproenic acid amides are effective for the treatment or prevention of headache disorders, such as migraines.

REFERENCES

U.S. Pat. No. 5,585,358, Bialer et al., issued Dec. 6, 1996.
Attal, N. 1999, Mechanism of action and rationale for use of antiepileptic drugs in: International Congress and Symposium Series 241 The Royal Society of Medicine Press Limited Ed. J M Pellock.
Handbook of Pharmaceutical Excipients, 2$^{nd}$ ed., A. H. Kibbe, Ph.D., ed., American Pharmaceutical Association and Pharmaceutical Press, Washington, D.C., 2000.
International Headache Society, 1988.
Kim, S. H. and Chung, J. M., 1992, Pain 50: 355-363.
Lehman, K., Acrylic Coatings in Controlled Release Tablet Manufacture, Manufacturing Chemist and Aerosol News, 1973, 39.
Lehman, K., Programmed Drug Release from Oral Program Forms, Pharma. Int., vol. ISS 3, 1971, 34-41.
Moskowitz, M. A. and Cutrer, F. M., Sumatriptan: a receptor-targeted treatment for migraines. Ann. Rev. Med., 1993: 44:145-154.
Silberstein, S. D. et al., 1998, Headache in Clinical Practice, Pub. Isis Medical Media, Oxford.
Suzzi, M. C. and Moskowitz, M. A., The Antimigraine Drug, Sumetriptan (GR43175), Selectively Blocks Neurogenic Plasma Extravasation from Blood Vessels in Dura Mater, 1990, Br. J. Pharmcol., 99: 202-206.
Tremont-Lukats, I. et al., Anticonvulsants for Neuropathic Pain, Drugs, 2000, 60: 1029.
Woolf, C. and Mannion, R., Neuropathic Pain: Aetiology, Symptoms, Mechanisms and Management, Lancet, 1999, 353: 1959.
The Merck Manual of Diagnosis and Therapy, 17$^{th}$ Ed., 1999, M. Beers and R. Berkow, eds., Merck Research Laboratories, Whitehouse Station, N.J.,
Principles of Neurology, 6$^{th}$ Ed., 1997, Adams, R. D. and Victor, M., McGraw-Hill, Inc., 148-159.

What is claimed is:

1. A method of treating a subject suffering from pain, comprising:
    periodically administering to the subject a therapeutically effective dose of 1,000 to 6,000 mg of a compound having the following structure

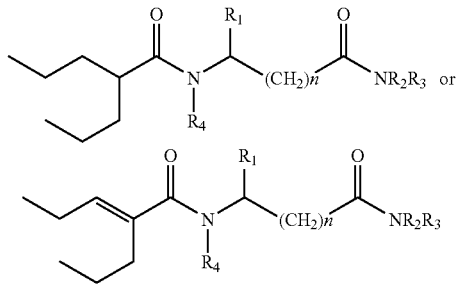

wherein $R_1$, $R_2$, $R_3$ and $R_4$ are each hydrogen and n is 0, and wherein the subject's pain is treated.

2. The method of claim 1, wherein the pain is acute pain.
3. The method of claim 1, wherein the pain is chronic pain.
4. The method of claim 1, wherein the pain is somatogenic pain.
5. The method of claim 4, wherein the somatogenic pain is neuropathic pain.
6. The method of claim 1, wherein the subject is a human being.
7. A method of treating a subject suffering from pain, comprising:
    periodically administering to the subject a pharmaceutical composition comprising
    a therapeutically effective dose of from 1,000 to 6,000 mg of a compound having the following structure

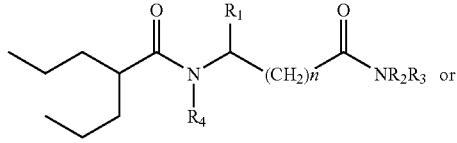

-continued

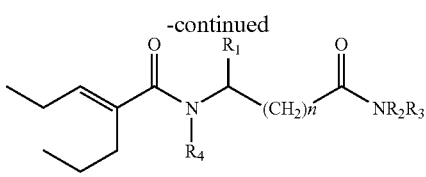

wherein $R_1$, $R_2$, $R_3$ and $R_4$ are each hydrogen and n is 0, and
a pharmaceutically acceptable carrier,
wherein the pain is neuropathic pain, a migraine or a headache disorder,
wherein the subject's pain is treated.

8. A method of treating a subject suffering from a headache disorder, comprising:
periodically administering to the subject a therapeutically effective dose of from 1,000 to 6,000 mg of a compound having the following structure

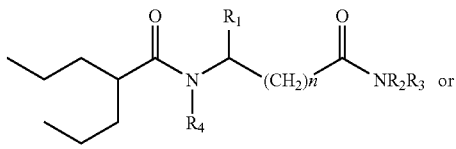 or

-continued

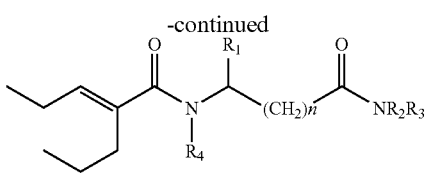

wherein $R_1$, $R_2$, $R_3$ and $R_4$ are each hydrogen, and n is 0,
wherein the headache disorder is treated.

9. The method of claim 8, wherein the headache disorder is a migraine, cluster headache, tension-type headache, or miscellaneous-type headache.

10. The method of claim 9, wherein the headache disorder is a cluster headache, tension-type headache, or miscellaneous-type headache.

11. The method of claim 4, wherein the somatogenic pain is cancer pain, postoperative pain, low back pain, complex regional pain syndrome, phantom pain, HIV pain, osteoarthritis pain or rheumatoid arthritis pain.

12. The method of claim 5, wherein the neuropathic pain is diabetic peripheral neuropathy, postherpetic neuralgia, or trigeminal neuralgia.

\* \* \* \* \*